United States Patent [19]

Namatame et al.

[11] Patent Number: 5,554,844

[45] Date of Patent: Sep. 10, 1996

[54] PASSBAND-ADJUSTABLE PHOTO-DETECTOR FOR INVERSE PHOTOEMISSION SPECTROSCOPY

[75] Inventors: Hirofumi Namatame, Higashihiroshima; Masaki Taniguchi, Hiroshima, both of Japan

[73] Assignee: Hiroshima University, Hiroshima, Japan

[21] Appl. No.: 404,554

[22] Filed: Mar. 15, 1995

[30] Foreign Application Priority Data

Mar. 24, 1994 [JP] Japan .................. 6-053821

[51] Int. Cl.⁶ .............. G01N 21/00; G02F 1/01; H01L 31/10
[52] U.S. Cl. .............. 250/207; 250/458.1; 250/459.1; 250/372
[58] Field of Search ........................ 250/207, 214 VT, 250/214 R, 214.1, 310, 307, 306, 372, 458.1, 459.1; 313/93, 528, 532, 533, 539

[56] References Cited

U.S. PATENT DOCUMENTS

| | | | |
|---|---|---|---|
| 3,712,700 | 1/1973 | Sommer | 445/13 |
| 5,120,965 | 6/1992 | Suga et al. | 250/372 |
| 5,340,976 | 8/1994 | Taniguchi et al. | 250/207 |

FOREIGN PATENT DOCUMENTS

| | | |
|---|---|---|
| 0475305 | 3/1992 | European Pat. Off. . |
| 0562874 | 9/1993 | European Pat. Off. . |

*Primary Examiner*—Edward P. Westin
*Assistant Examiner*—John R. Lee
*Attorney, Agent, or Firm*—Spencer & Frank

[57] ABSTRACT

A passband-adjustable photo-detector for inverse photoemission spectroscopy, in which an electron beam from an electron gun is applied onto a sample and a light reflected therefrom is converged, so as to effect photo-detection, wherein said photo-detector comprises a photo-electron multiplier, a LiF monocrystal window and a $CaF_2$ monocrystal window individually deposited with a KCl thin film in the front of a photo-electron multiplier in the photo-detector, wherein said windows means are provided for arbitrarily setting the temperature from the vicinity of liquid nitrogen temperature to the order of 150° C., a photo-electron multiplier having a first dinode deposited a KCl thin film on a surface thereof said photo-electron multiplier, and an output of the photo electron multiplier is connected with a pulse counter circuit through an amplifier, so as to measure anyone selected from the group consisting of light absorption property, window transmissibility and sensitivity as a bandpass filter.

8 Claims, 8 Drawing Sheets

FIG_1
PRIOR ART
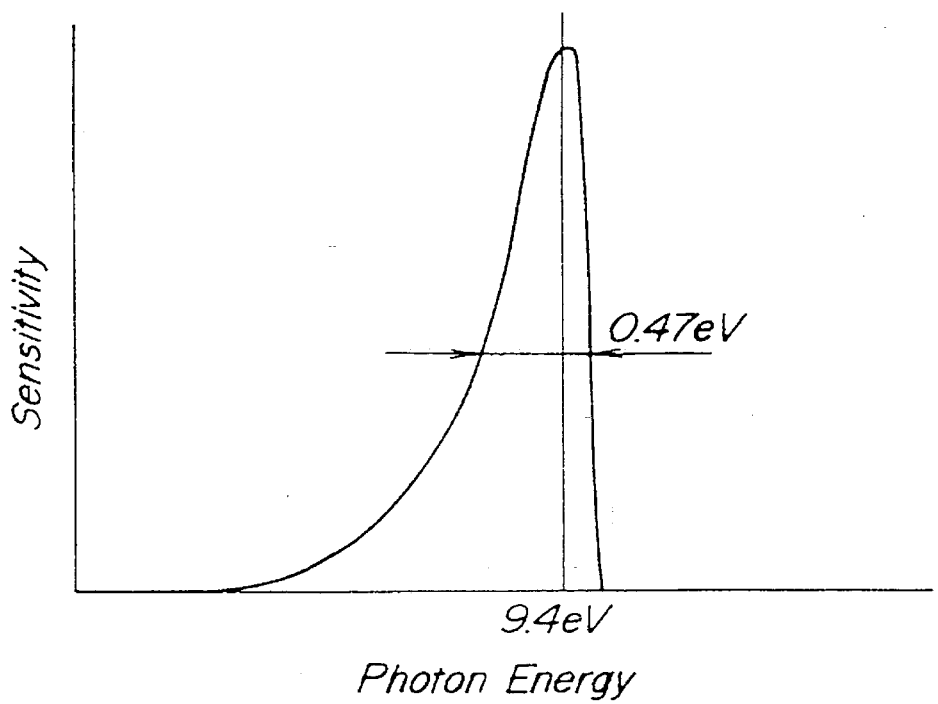
FIG_2
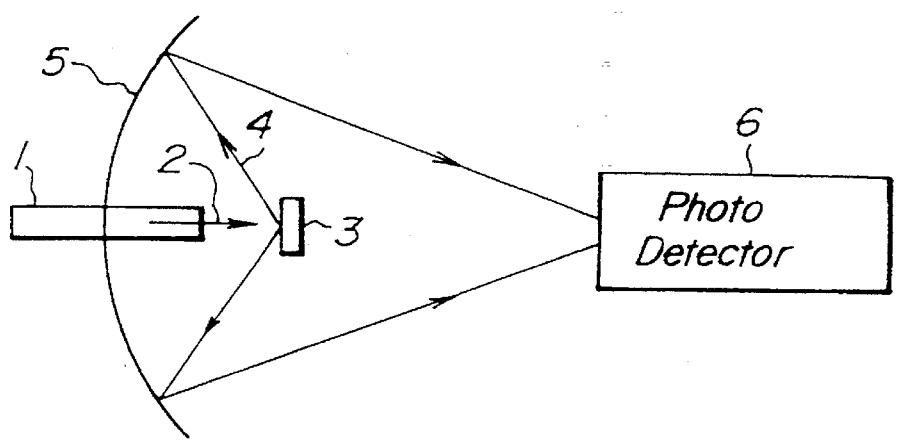

FIG_5
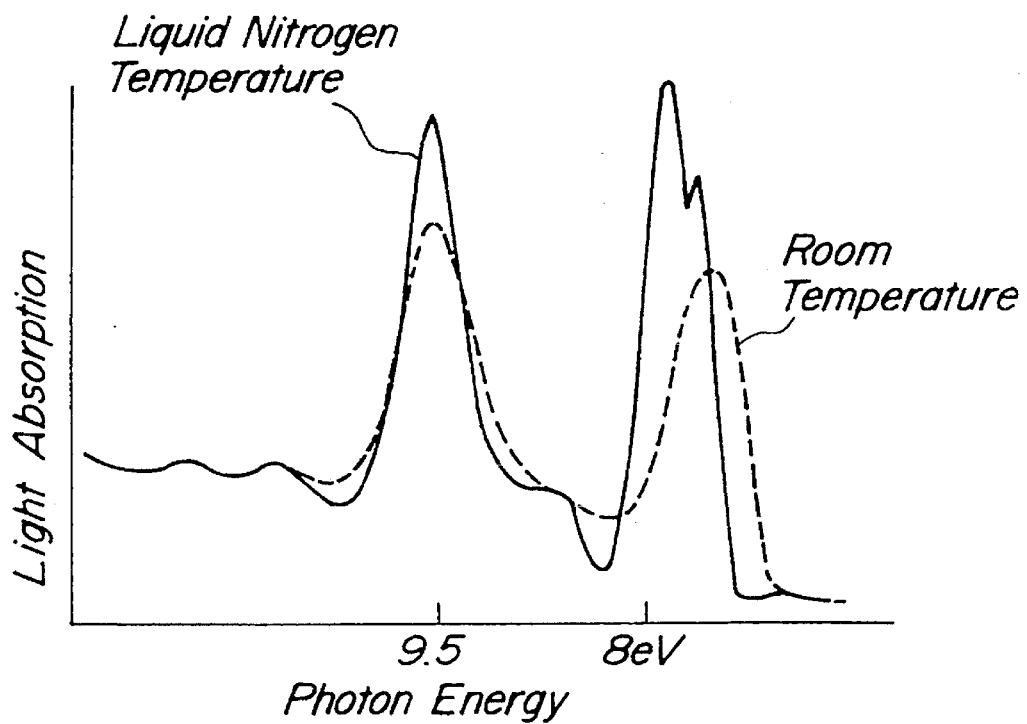
FIG_6
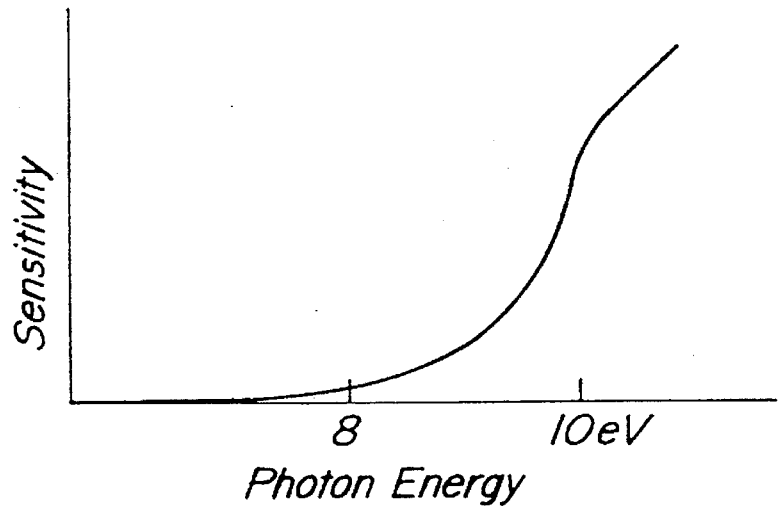

FIG_9A
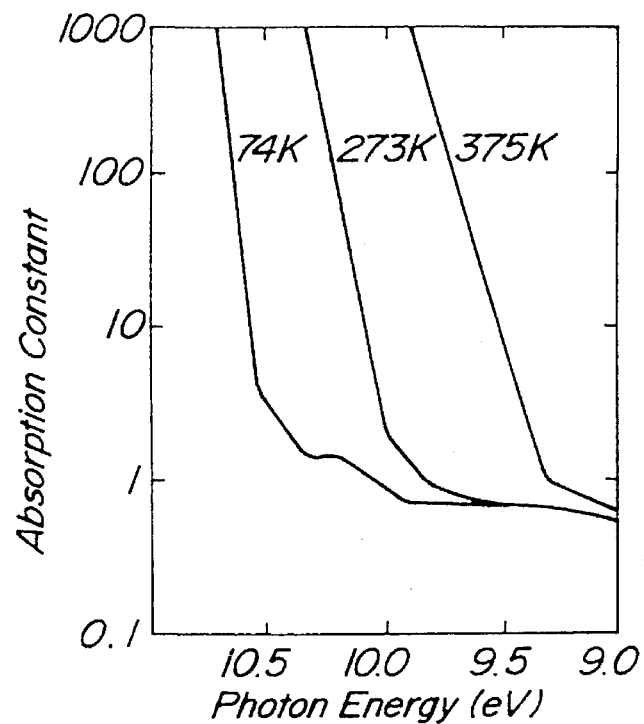
FIG_9B
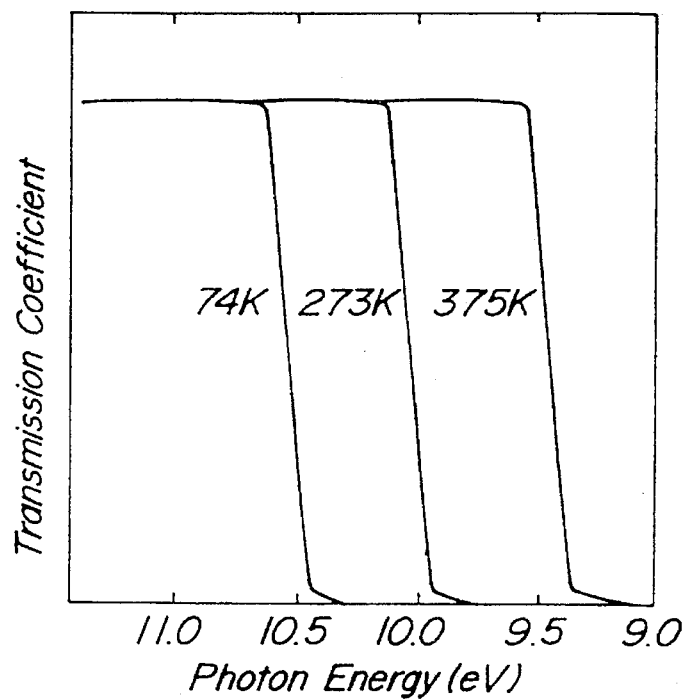

FIG_10
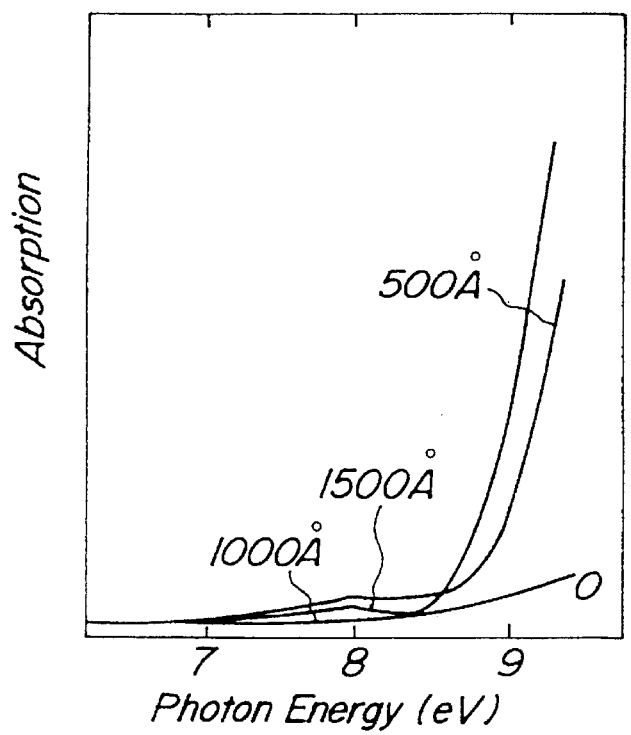
FIG_11
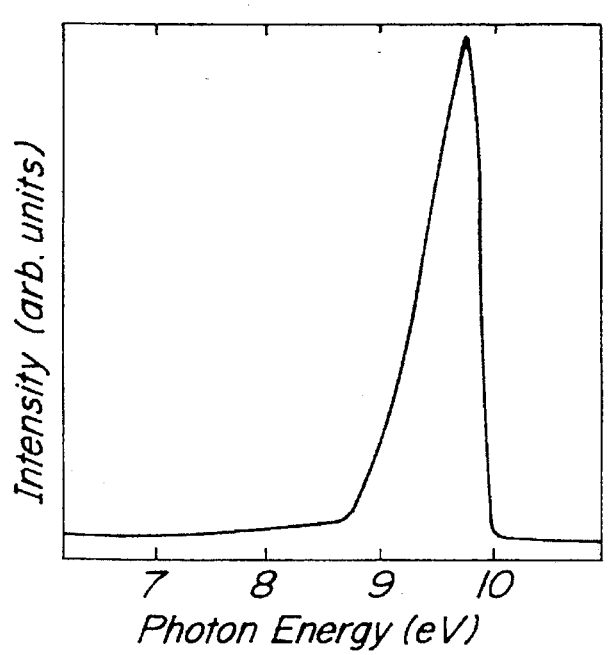

FIG_12
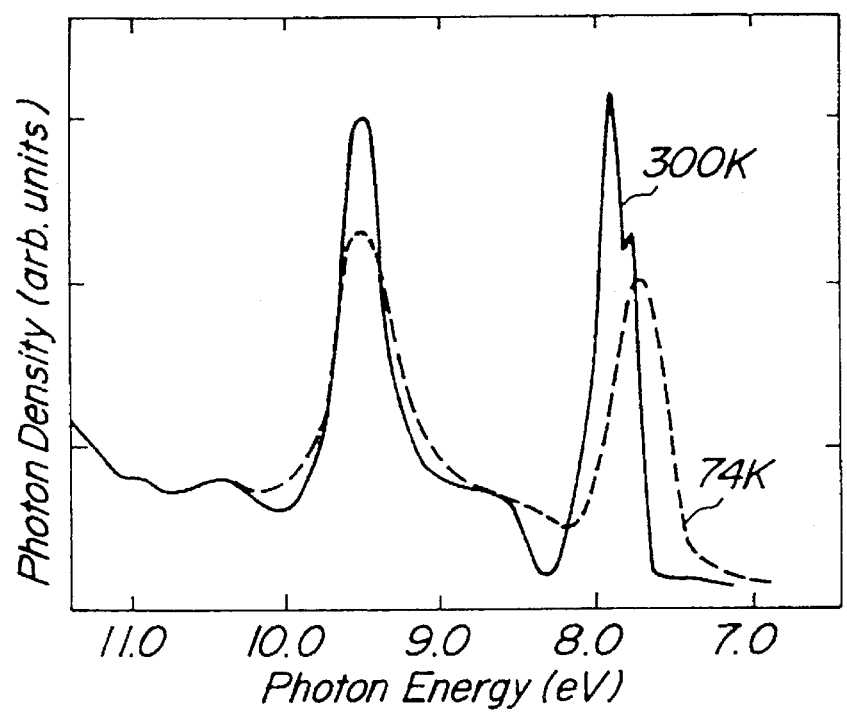
FIG_13
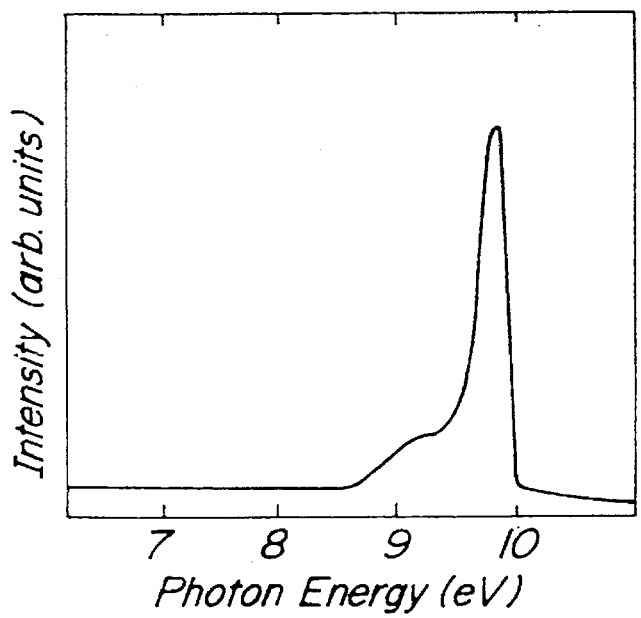

PASSBAND-ADJUSTABLE PHOTO-DETECTOR FOR INVERSE PHOTOEMISSION SPECTROSCOPY

BACKGROUND OF THE INVENTION

1. Field of the Invention

The present invention relates to a passband-adjustable photo-detector for inverse photoemission spectroscopy, which belongs to the technical fields of electron technology and photon technology and is used for a high resolution inverse photoemission spectroscope.

2. Related Art Statement

A bandpass filter type photo-detector for inverse photoemission spectroscopy is formed of a simple combination of low-cut and high-cut filters. In a recently developed photo-detector having excellent properties, the low-cut filter is a photoelectron multiplier provided with Cu-BeO having a KCl thin film deposited on a surface thereof as the first dynode, while the high-cut filter is a $SrF_2$ monocrystal window having a sensitivity property of central energy at 9.40 eV and a half value width of 0.47 eV, as shown in FIG. 1.

This bandpass filter type photo-detector is characterized by a structure that is simple and an operational stability that is high. However, the obtainable resolution thereof is no more than 0.47 eV at most.

Photoemission spectroscopy and inverse photoemission spectroscopy are means for directly observing occupied and unoccupied electronic states of energy in a material, respectively, and hence have a complementary relation with each other. The presently standardized resolution of photoemission spectroscopy is on the order of 0.3 eV. The investigation of occupied and unoccupied electronic states of energy with a precision of the same order by the employment of photoemission and inverse photoemission spectroscopies respectively is extremely desirable for the research of materials. It is necessary for the realization thereof to narrow the bandwidth of the bandpass filter type photo-detector into the order of 0.3 eV.

In general, when the resolution is increased, the detection sensitivity is lowered. This is also true of the bandpass filter type photo-detector for photoemission spectroscopy. If the surface of the material to be measured is unstable in vacuum, an experiment wherein signals are accumulated for a long time is impractical. In this case, it is required to raise the detection sensitivity at the sacrifice of resolution. However, it is not possible to vary the width of the passband of the conventional bandpass filter type photo-detector during the experiment. Accordingly, it is required for achieving high resolution to provide a measuring apparatus comprising two kinds of detectors, a high resolution detector, even if the detection sensitivity is somewhat low, and a high sensitivity detector.

Photoemission spectroscopy and inverse photoemission spectroscopy provide information relating to occupied and unoccupied electronic states respectively, so that the whole aspect of the electronic states of a material cannot be clarified until both kinds of information are combined. The resolution of conventional photoemission spectroscopy is on the order of about 0.3 eV, while the resolution of conventional inverse photoemission spectroscopy is on the order of about 0.5 eV. Accordingly, it is necessary for comparing and investigating respective data from both of these spectroscopies to provide comparable resolutions to each. Inverse photoemission spectroscopy is a method for clarifying the unoccupied electronic state of a material by taking notice of a certain single energy component of light emitted from the surface of a sample which has a monochromatized electron beam applied thereto, and by observing the intensity of the emitted light as a function of the energy of the noticed electron beam. The energy width of the electron beam is defined by the expansion of a thermo-electron in the electron source which is about 0.25 eV. On the other hand, the width of the pass band of the bandpass filter type photo-detector is conventionally about 0.47 eV and has been improved to 0.35 eV by recent technical developments. However, to obtain resolution comparable with that of photoemission spectroscopy, it is necessary to narrow the width of the passband of the photodetector to the order of the electron beam width of 0.25 eV.

In general, in photoemission spectroscopy, when the resolution is raised, the detection sensitivity is lowered. This is also true of the bandpass filter type photo-detector for inverse photoemission spectroscopy, so that, when the half value width of the detector is narrowed, the detection sensitivity is lowered and hence a longer time is required for the measurement. On the other hand, when the half value width is widened, the sensitivity is raised and hence the measurement is carried out in a shorter time. In general, whether the resolution or the sensitivity is preferential, is decided by the limitation of the time required for the measurement and whether the material to be measured is stable or not in super high vacuum wherein the inverse photoemission spectroscopy is effected.

SUMMARY OF THE INVENTION

The present invention provides technology for continuously varying the resolution obtained with inverse photoemission spectroscopy from a value higher than that obtained with the usual photoemission spectroscopy to a lower value, so as to necessarily exhibit high power in a practical high resolution experiment.

According to the present invention, it can be determined whether resolution or sensitivity is preferential by electrically controlling the half value width of the bandpass filter without any change of the experimental apparatus during the experiment, so that the time required for the experiment can be reduced and a measurement can be made of a material for which a long time measurement is not suitable by raising the sensitivity at the partial sacrifice of resolution, thereby making a significant contribution to research into the properties of materials.

The present invention relates to a passband-adjustable photo-detector for inverse photo emission spectroscopy, in which an electron beam from an electron gun is applied onto a sample and a light reflected therefrom is converged into a photo-electron multiplier, so as to effect photo-detection, said photo-detector comprising a photo-electron multiplier, a LiF monocrystal window, and a $CaF_2$ monocrystal window respectively deposited with KCl thin film being provided in the front of a photo-electron multiplier, wherein said windows are provided for arbitrarily setting the temperature from approximately liquid nitrogen temperature to a temperature on the order of 150° C., a first dynode having a KCl thin film deposited on the surface thereof, wherein an output of the photo-electron multiplier is connected with a pulse counter circuit through an amplifier, so as to measure any property selected from the group consisting of light absorption property, window transmissibility and sensitivity as a bandpass filter for inverse photoemission spectroscopy.

BRIEF DESCRIPTION OF THE DRAWINGS

For better understanding of the invention, reference is made to the accompanying drawings, in which:

FIG. 1 is a diagram showing a property of a conventional bandpass filter type photo-detector for inverse photoemission spectroscopy;

FIG. 2 is a schematic diagram showing the principle of a passband-adjustable photo-detector for inverse photoemission spectroscopy according to the present invention;

FIG. 5 is a diagram showing a light absorption property of a KCl thin film in the photo-detector according to the present invention;

FIG. 6 is a diagram showing a sensitivity property of a photo-electron multiplier deposited with a KCl thin film in the photo-detector according to the present invention;

FIGS. 9A and 9B are diagrams showing temperature dependency of the absorption factor and the transmission coefficient of photon energy at 74K, 273K and 375K respectively;

FIG. 10 is a diagram showing the photoemission absorption property of a KCl deposited thin film at 1000 Å, 1500 Å and 500 Å in the photo-detector according to the present invention;

FIG. 11 is a diagram showing a bandpass filter characteristic presenting an asymmetric peak structure of the combination of a $CaF_2$ monocrystal window and a KCl deposited first dynode of the photo-electron multiplier in the photo-detector according to the present invention;

FIG. 12 is a diagram showing a transmission property of a LiF monocrystal window deposited with a KCl thin film in the photo-detector according to the present invention;

FIG. 13 is a diagram showing a transmission property of a LiF monocrystal window used for a substrate of a KCl deposited thin film in the photo-detector according to the present invention.

Figure 3:
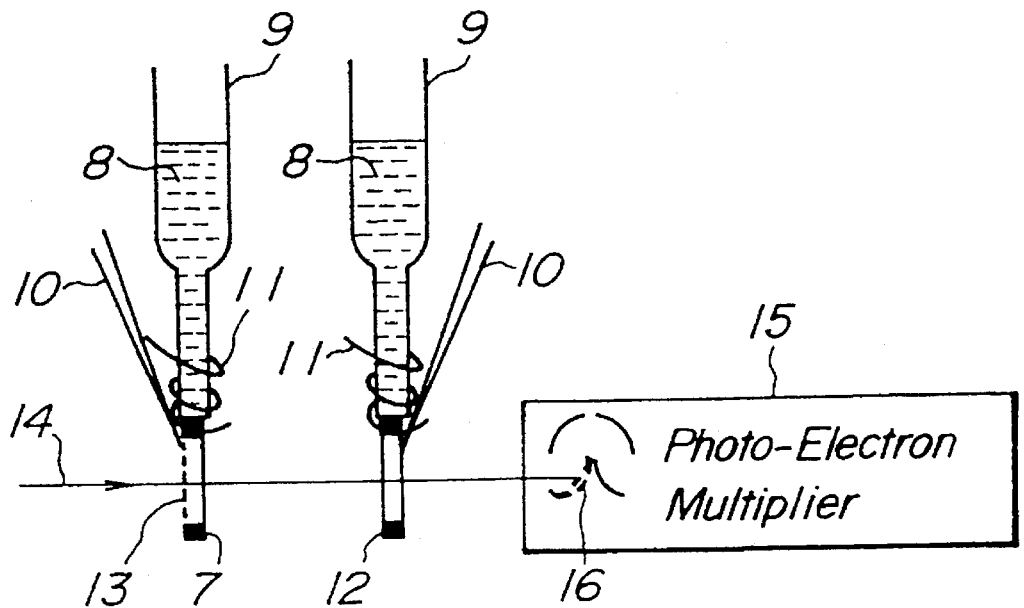
FIG. 3 is a diagram showing a principal arrangement of an embodiment of the photo-detector according to the present invention.

Throughout different views of the drawings; 1 is an electron gun, 2 is an electron beam, 3 is a sample, 4 is a reflected light, 5 is a converging mirror, 6 is a photo-detector, 7 is a LiF monocrystal window deposited with a KCl thin film, 8 is liquid nitrogen, 9 is a cryostat, 10 is a thermo-couple, 11 is a heater, 12 is a $CaF_2$ monocrystal window deposited with a KCl thin film, 13 is a KCl thin film, 14 is an incident light beam, 15 is a photo-electron multiplier, and 16 is a first dynode.

DESCRIPTION OF THE PREFERRED EMBODIMENT

The present invention is explained hereinafter in detail with respect to the attached drawings.

FIG. 2 shows the principle of operation of an inverse photoemission spectroscope, in which 1 is an electron gun, 2 is an electron beam emitted therefrom, and 3 is a sample. The electron beam 2 emitted from the electron gun impinges on the sample 3. Light 4 emitted from the sample 3 is converged by a converging mirror 5, so as to irradiate a photo-detector 6.

FIG. 3 shows the principle of operation of the passband width-adjustable photo-detector for inverse photoemission spectroscopy according to the present invention. In FIG. 3, the principal structure of an inverse photoemission spectroscope comprised in the photo-detector 6 as shown in FIG. 2 is illustrated. In FIG. 3, 7 is a LiF monocrystal window, on a surface of which a KCl thin film 13 is deposited with 100 Å thickness. The LiF monocrystal window 7 is refrigerated at a temperature in the vicinity of the temperature of liquid nitrogen by means of a cryostat 9, which accommodates liquid nitrogen 8 and additionally comprises thermo-couple 10 and heater 11, so as to provide a temperature adjusting arrangement.

$CaF_2$ monocrystal 12 is supported within a cryostat 9 accommodated with liquid nitrogen 8 in the same way as the LiF monocrystal window and is also provided with a temperature adjusting arrangement comprising a thermo-couple 10 and heater 11.

An incident light 14 shown in FIG. 3 is the same as the incident light projected into the photo-detector 6 as shown in FIG. 2. The incident light 14 is applied on a first dynode 16, on a surface of which a KCl thin film is deposited at 1000 Å thickness, of a photo-electron multiplier 15 of the solar blind type (e.g. HTV:R-595), through the LiF monocrystal window 7 and the $CaF_2$ monocrystal window 12 refrigerated at the vicinity of liquid nitrogen temperature.

The incident light into the photo-detector 6 passes through a KCl thin film coated LiF monocrystal window 7 and a KCl thin film coated $CaF_2$ monocrystal window 12.

Figure 4:
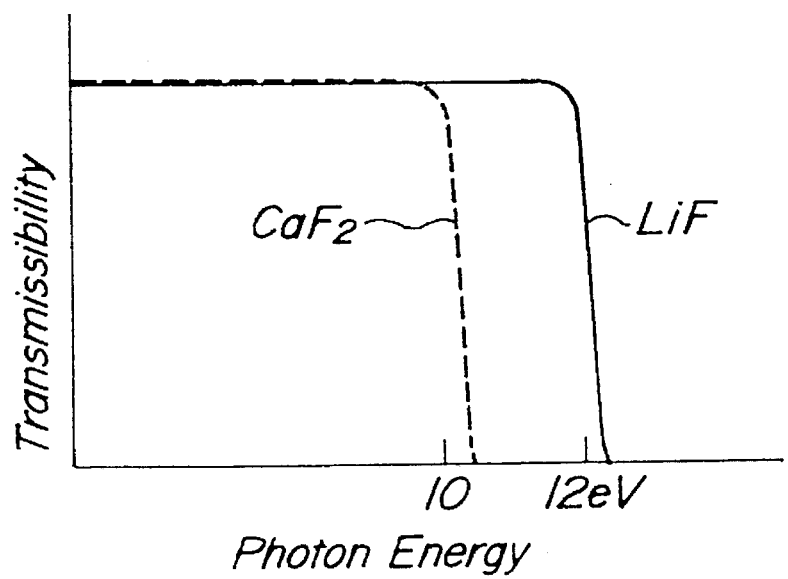
FIG. 4 is a diagram showing the energy dependency of transmissibility of the window in the photo-detector according to the present invention.

The cutoff energy of the LiF monocrystal window 7 is 12 eV at room temperature, while the cutoff energy of the $CaF_2$ monocrystal window 12 is 10 eV at room temperature. Consequently, as is apparent from the energy dependency of the transmission factor of these windows as shown in FIG. 4, light having energy more than about 10 eV cannot pass through these windows.

As shown in FIG. 5, the KCl thin film has a light absorption property which presents high and sharp peaks approximately at 9.5 eV and 8.0 eV. This light absorption property is emphasized by refrigeration, and hence these peaks become still higher and sharper. According to this effect, the same result as is obtained by a 150 Å thickness of KCl at room temperature can be obtained by an about 100 Å thickness under refrigeration. In addition, the light absorption of a KCl thin film at the vicinity of 9.8 eV is somewhat reduced at a very low temperature relative to that at room temperature, so that such a condition as light transmission is readily obtained in the vicinity of 9.8 eV just before the cutoff energy of the $CaF_2$ monocrystal window, while said condition is difficult to obtained in the vicinity of 9.5 eV.

The incident light successively passing through LiF monocrystal window 7 and $CaF_2$ monocrystal window 12 is applied to the photo-electron multiplier 15 comprising the first dynode 16 of the photo-detector 6. The incident light is applied to the KCl thin film on the surface of dynode 16, a photo-electron is emitted from the surface of said thin film, and is amplified by the photo-electron multiplier 15. As shown in FIG. 6, the photoemission of a KCl thin film 1000 Å thick appears about a 8 eV and is suddenly increased at the vicinity of 9 eV. The combination of LiF monocrystal window 7 and CaF$_2$ monocrystal window 12 provides a high cut filter having a bandpass structure at the vicinity of the cutoff energy of the CaF$_2$ monocrystal window of about 10 eV, while the combination of the photo-electron multiplier 15 and the first dynode 16 provides a low cut filter having high sensitivity in an energy range exceeding the vicinity of 9 eV.

Figure 7:
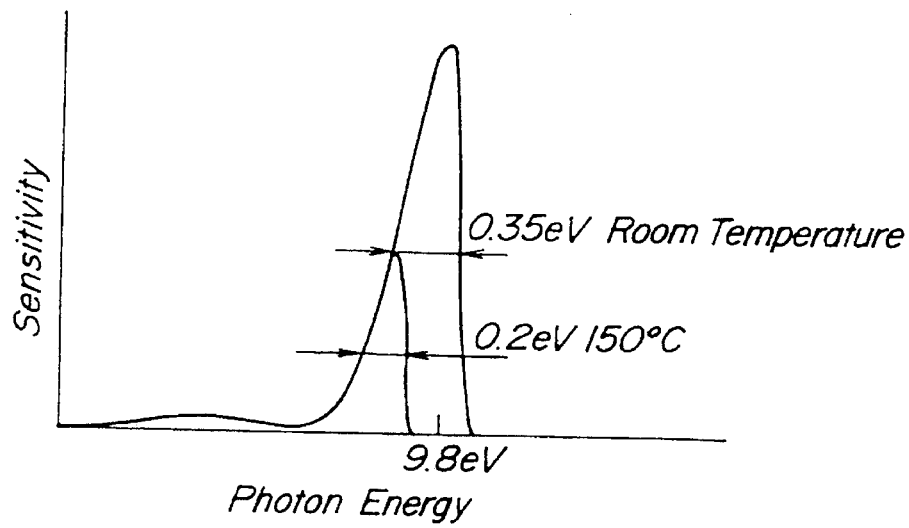
FIG. 7 is a diagram showing a property of the bandpass filter in the bandwidth adjustable photo-detector according to the present invention.

Consequently, the combination of the photo-electron multiplier 15, the first dynode 16, the LiF monocrystal window 7 and the CaF$_2$ monocrystal window 12 provides a bandbass property having a peak at 9.8 eV. The temperature of the CaF$_2$ monocrystal window can be varied from a low temperature, that is, liquid nitrogen temperature to a high temperature, that is, about 150° C., and further can be maintained at an arbitrary temperature. The cutoff energy of the CaF$_2$ monocrystal window 12 is about 10 eV at room temperature, and is shifted toward the high energy side as the temperature is lowered, and toward the low energy side as the temperature is raised. For instance, when the temperature is raised to 150° C., the cutoff energy is transferred to the low energy side of about 0.3 eV. The property of the higher energy side of the bandpass filter type photoemission detector is defined by the cutoff property of CaF$_2$ monocrystal window 12, so that the bandwidth is varied by the temperature variation of the window 12. As shown in FIG. 7, the bandwidth of 0.35 eV at room temperature is narrowed to about 0.2 eV at 150° C. Thus, an arbitrary bandwidth can be set in this temperature range.

An actual example of the passband adjustable photodetector for inverse photoemission spectroscopy according to the present invention will be described hereinafter.

Figure 8:
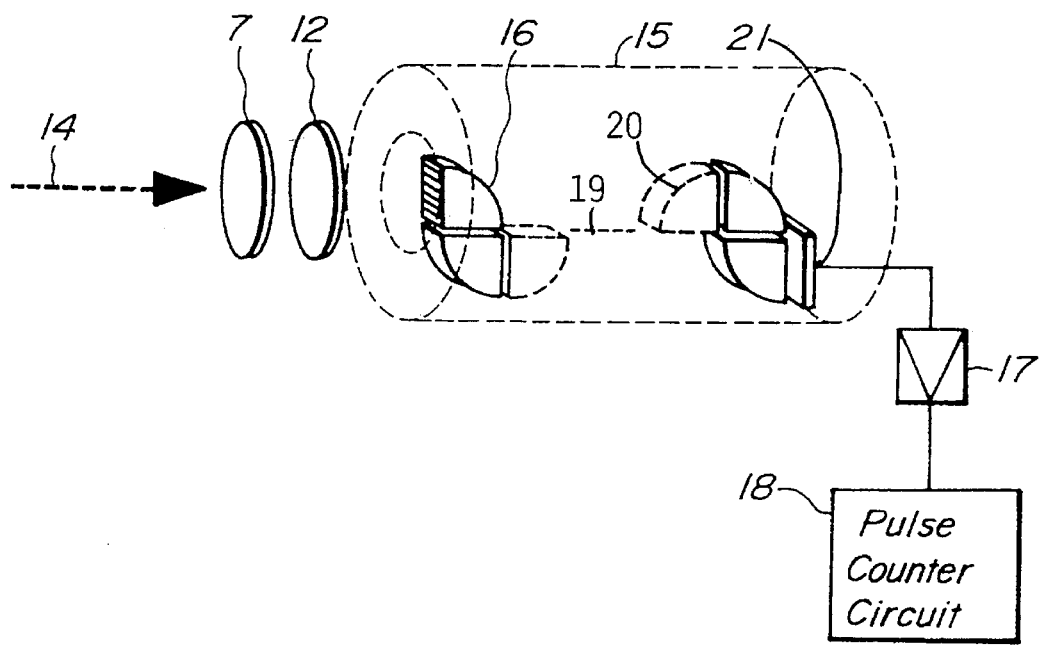
FIG. 8 is a diagram showing a principal practical arrangement of the photo-detector according to the present invention.

The construction of the photo-detector 6 is shown in FIG. 8. FIG. 8 shows an example of an actual arrangement of the photo-detector 6 as shown in FIG. 3, in which 14 is the incident light, 7 is a LiF monocrystal window deposited with a KCl thin film 100 Å thick, 12 is a CaF$_2$ monocrystal window, 15 is a photo-electron multiplier, 16 is a first dynode deposited with a KCl thin film 1000 Å thick, 17 is an amplifier connected to an output of the multiplier 15 and 18 is a pulse counter circuit.

The photoemission of the CaF$_2$ monocrystal window presents a lowpass filter property. That is, the absorption coefficient is abruptly increased at the vicinity of 10 eV wherein the exciton absorption appears, and, in a region exceeding such a cutoff energy, the light transparency is lost, while, in a region below this cutoff energy, the CaF$_2$ monocrystal window presents almost flat light transparency.

The cutoff energy is caused at the energy level wherein exciton absorption appears, so that this energy level is varied by the crystal temperature. In practice, this energy level wherein the exciton absorption appears is varied as shown in FIGS. 9A and 9B, by the crystal temperature variation from the liquid nitrogen temperature (74K) to 375K.

However, even in this case in which the crystal temperature is varied, the transparency property in the energy region below the absorption limit is flat, so as to surely realize a variable cutoff lowpass filter.

Next, the photo-detection property of the photo-electron multiplier 15 comprising the first dynode 16 having a KCl thin film 1000 Å in thickness will be explained. The first dynode 16 consists of CuBe-O and the photo-electron absorption property thereof presents finite values in the vicinity of an energy level of about 6 eV and, as a result, presents an abrupt increase in absorption with an increase of photo-energy. This photo-electron absorption property is varied by depositing a KCl thin film on the surface of the first dynode 16, while the absorption further abruptly increases together with the increase of photo-energy as shown in FIG. 10. This is because of the reflection of the photoelectron absorption property of the KCl thin film consisting of an ion crystal which is a proper insulator. Thus, it results that the KCl thin film is electrically charged by deriving photo-electrons therefrom. The photo-electron absorption is reduced by depositing a thick KCl thin film, and is also reduced by depositing a too thin KCl thin film because of the reduced contribution thereof, so that it is required to select the most suitable thickness thereof.

When the photo-electron absorption is measured as the increase of thickness of the KCl thin film, it appears that this absorption is almost simply increased until the vicinity of 1000 Å thickness as shown in FIG. 10, and represents the tendency of saturation with a further increase of thickness. According to further detailed observation of film thickness dependency of the photo-electron absorption, it appears that the absorption at the vicinity of 8 eV is reduced at the vicinity of 1000 Å thickness. Accordingly, it is possible to realize such a property that the photo-electron absorption is reduced at the vicinity of 8 eV and is suddenly increased over 9 eV by depositing a KCl thin film of 1000 Å thickness.

The photo-electrons 19 emitted from the first dynode 16 are amplified by about $10^6$ through a plural electrode 20 for secondary electron multiplication and are collected by a collector 21. The intensity of the collected electrons is observed by the pulse counter circuit 18 after amplification through amplifier 17 as a preamplifier. This property of photo-electron multiplier 15 represents a highpass filter property as to the photo-energy, so that the cutoff energy thereof is defined by the increase of the photo-electron absorption of the KCl thin film at the vicinity of about 9 eV.

According to the combination of CaF$_2$ monocrystal window 12 and the first dynode 16 of the photo-electron multiplier 15 on which the KCl thin film is deposited, that is, the combination of the lowpass and highpass filters, it is possible to realize a bandpass filter, the difference of respective cutoff energies of these filters corresponding to the passband width. However, the practical characteristics do not represent an ideal step function as the filter property but only gradual variations in the vicinities of the respective cutoff energies, so that the obtainable bandpass characteristic represents an asymmetric peak structure on the basis of reflections of respective rise-up properties, as shown in FIG. 11.

The cutoff characteristic of the lowpass filter, which depends on exciton absorption, is sharp for a good quality CaF$_2$ monocrystal window, while the cutoff characteristic of the highpass filter, having a photo-electron absorption property reflecting the interband transition of the KCl thin film, is comparatively gradual. Thus, it is necessary to narrow the half value width of the bandpass filter to improve the characteristics of the aforesaid highpass filter. Accordingly, it is necessary to consider the LiF monocrystal window 7 deposited with a KCl thin film.

The transmission property of a KCl thin film represents sharp exciton absorption at the vicinity of 9.5 eV, the energy level of which is somewhat lower than the cutoff of the low pass filter and corresponds to the cutoff of a highpass filter as shown in FIG. 12.

An improved highpass filter can be realized by combining the KCl thin film with the first dynode 16 of the aforesaid photo-electron multiplier 15. On the other hand, LiF monocrystal window 7 is transparent below the vicinity of 11 eV and hence can be used as the substrate for depositing a KCl thin film. Accordingly, a bandpass filter property having a central energy of 9.9 eV and a half value width of 0.37 eV as shown in FIG. 13 can be realized by combining these three elements.

Figure 14:
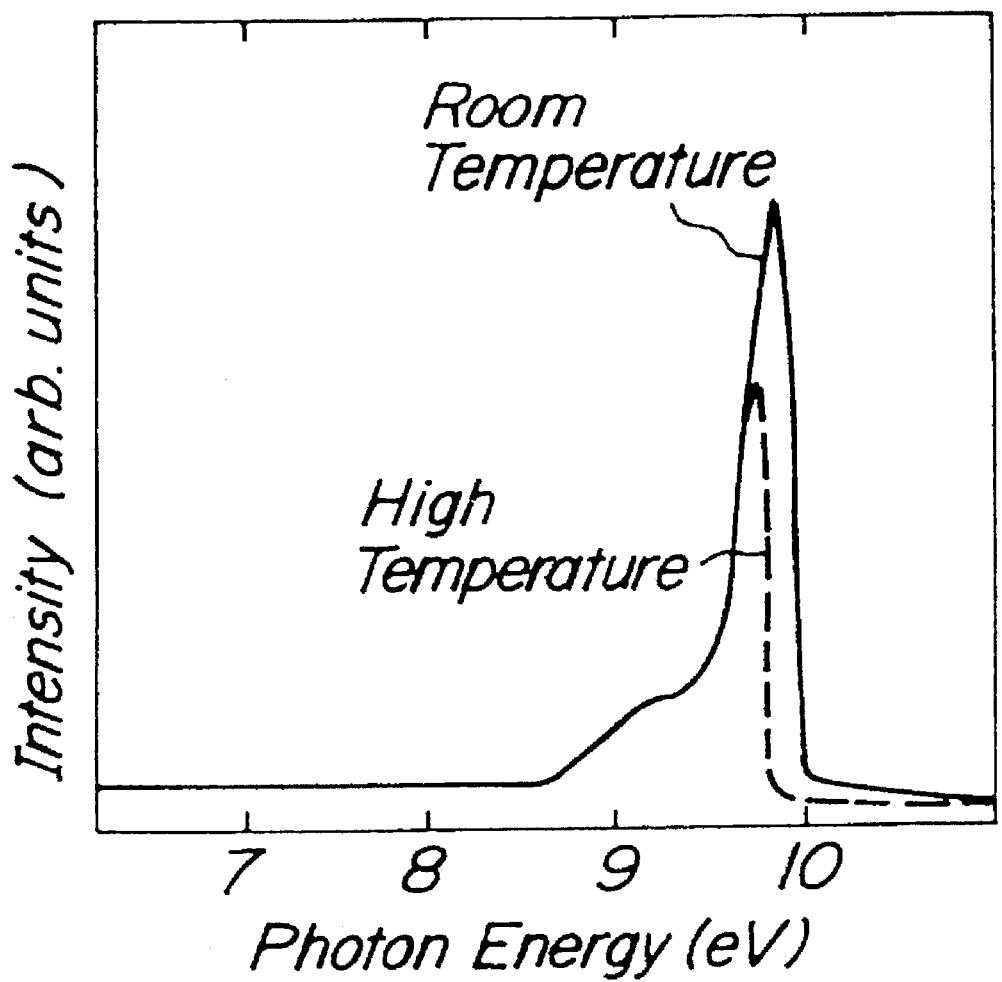
FIG. 14 is a diagram showing temperature dependency of a bandpass filter in the photo-detector according to the present invention.

$CaF_2$ monocrystal window 12 represents an almost ideal lowpass filter property, the cutoff of which is defined by the crystal temperature. When $CaF_2$ monocrystal window 12 is refrigerated toward a low temperature of 74K, the cutoff energy is shifted toward the high energy side, while, when it is heated to a high temperature, the cutoff energy is shifted toward the low energy side, as is apparent from FIGS. 9A and 9B. Accordingly, the property of the bandpass filter represents the variation of property, which corresponds to the variation of high energy cutoff. When $CaF_2$ monocrystal window 12 is heated at a high temperature of about 375K, the bandwidth is increased, while, when it is refrigerated at a low temperature of 74K, the bandwidth is reduced, as shown in FIG. 14. In addition to the variation of bandwidth, a variation of central energy level also results. However, the usage for measuring inverse photoemission spectroscopy can be made possible by calibration as a function of temperature.

The deterioration of measurement sensitivity is unavoidably caused by the measurement with high resolution, so that much more time than that with the usual resolution is required. In making a practical measurement, although a measurement with high resolution is preferable, it is required to raise the sensitivity at a certain sacrifice of the resolution in relation to measurement time duration, and hence the bandwidth adjustable photo-detector 6 according to the present invention becomes useful. This photo-detector 6 is made applicable by the previous calibration. This means that a novel property can be obtained by additionally providing a temperature adjustable structure such as a thermo-couple 10 and a heater 11 as shown in FIG. 3 in the same structure as the photo-detector 6 afforded with high resolution by utilizing a window deposited with a KCl thin film.

The same property can be theoretically obtained by also directly depositing a KCl thin film on the monocrystal window 12. However, under the condition such as the temperature adjustable structure is additionally provided so as to be heated, the possibility that a reaction between the KCl thin film, and the $CaF_2$ monocrystal window will cause trouble is high. Therefore, it is preferable to provide a LiF monocrystal window 7 for the substrate of the KCl thin film.

According to the present invention, the bandwidth of the bandpass filter used for the photo-detector can be continuously varied from the conventional bandwidth of 0.35 eV to a narrow bandwidth of 0.2 eV only by the simple method of heating a monocrystal window in the bandpass filter. In contrast, the bandwidth can be widened by refrigeration, so that a particularly widened bandwidth of about 0.9 eV can be attained at the temperature of liquid nitrogen. The wider the bandwidth, the higher the detection sensitivity, while the sensitivity is reduced with a narrow bandwidth. A case in which all materials should be measured with high resolution and long time expense is rare, while particular materials, for instance organic materials and materials having unstable surfaces should be measured with a time duration that is as short as possible. Furthermore, there is a certain case in which an entire sample is measured with low resolution and only a part thereof should be measured with high resolution. However, the photo-detector according to the present invention is efficient, because the resolution of the detector can be optionally set, although the setting range is restricted. The present invention has an industrial merit such that the measurement which conventionally necessitates plural apparatus in the prior art can be effected only by one apparatus according to the present invention.

In the bandpass filter type photo-detector for inverse photoemission spectroscopy of the present invention, a $CaF_2$ monocrystal window is used for the high cut filter, while for the low cut filter there is used a photo-electron multiplier having a sufficient sensitivity in an energy region exceeding that of a vacuum ultra-violet ray, i.e. an ultra-violet ray, having a short wavelength, which is transmitted under vacuum conditions so as to arrive at a desired distance. In addition to this fundamental arrangement, for improving the performance thereof, the low energy side performance of the bandpass filter is improved by depositing a KCl thin film on the LiF monocrystal window 7 and the $CaF_2$ monocrystal window 12 in the light transmission region, so as to utilize the absorption property inherent in a KCl thin film. Furthermore, a sensitivity raising material, that is, usually a KCl thin film is deposited on the photoemissive surface of the photo-electron multiplier. The present invention is featured in that, in view of the temperature dependency of the light absorption property of a $CaF_2$ monocrystal window and a KCl thin film, the optional setting of the passband width can be realized together with the improvement of bandpass width and sensitivity.

As to the light absorption property of the KCl thin film, as shown in FIG. 5, the absorption in the vicinity of 9.5 eV at low temperature is sharply increased and the absorption in the vicinity of 9.8 eV in the bandpass region is reduced, so as to facilitate light transmission. According to the increase of absorption at low temperature, the same absorption can be obtained through a thicker thin film. For instance, it is possible to reduce the film thickness from 150 Å at room temperature (in the prior art) to the order of 100 Å according to the present invention, and hence to facilitate light transmission within the bandpass region.

The temperature dependency of the cutoff energy of the $CaF_2$ monocrystal window is shifted toward the low energy side at a high temperature, while shifted toward the high energy side at low temperature. The sharpness of absorption and the variation of transmissibility in the transmissible region are negligibly small. As is apparent from FIG. 7, the bandwidth can be optionally set by the temperature control of the $CaF_2$ monocrystal window, so as to facilitate the desired measurement.

This bandwidth adjustable structure can be applied also to a bandpass filter type photo-detector employing other than a $CaF_2$ monocrystal window, that is, anyone selected among $SrF_2$, $MgF_2$ and LiF monocrystal windows can be used as the high cut filter.

What is claimed is:

1. For use in inverse photo-emission spectroscopy wherein an electron gun directs an electron beam on to a sample, a pass-band adjustable photo-detector receiving light emitted by said sample when said electron beam impinges thereon, said photo-detector comprising:

a photo-electron multiplier including a dynode having a first KCl film deposited thereon, and a collector for collecting electrons emitted by said dynode;

a LiF monocrystal window and a $CaF_2$ monocrystal window interposed between the sample and said dynode, said LiF window having a second KCl film deposited thereon, light emitted by the sample being transmitted through said LiF and $CaF_2$ windows to impinge on said dynode;

temperature adjusting means for setting the temperature of said monocrystal windows between the temperature of liquid nitrogen and 150° C.; and output means coupled to an output of said photo-electron multiplier for measuring the intensity of the electrons collected by said collector.

2. A photo-detector as defined by claim 1 wherein said $CaF_2$ monocrystal window has a third KCl film deposited thereon.

3. A photo-detector as defined by claim 1 wherein the dynode of said photo-electron multiplier having said first KCl film deposited thereon functions as a high pass filter and said $CaF_2$ monocrystal window functions as a low pass filter, said combination providing a bandpass filter.

4. A photo-detector as defined by claim 2 wherein the dynode of said photo-electron multiplier having said first KCl film deposited thereon functions as a high pass filter and said $CaF_2$ monocrystal window functions as a low pass filter, said combination of filters providing a bandpass filter.

5. A photo-detector as defined by claim 1 wherein said output means comprises a pulse counter circuit coupled to said photo-electron multiplier by an amplifier.

6. For use in inverse photo-emission spectroscopy wherein an electron gun directs an electron beam on to a sample, a pass-band adjustable photo-detector receiving light emitted by said sample when said electron beam impinges thereon, said photo-detector comprising:

a photo-electron multiplier including a dynode having a first KCl film deposited thereon, and a collector for collecting electrons emitted by said dynode;

a first monocrystal window consisting of LiF, said first monocrystal window having a second KCl film deposited thereon;

a second monocrystal window, said second monocrystal window consisting of a material selected from the group consisting of LiF, $CaF_2$, $SrF_2$ and $MgF_2$, said first and second monocrystal windows being interposed between the sample and said dynode, light emitted by the sample being transmitted through said first and second monocrystal windows to impinge on said dynode;

temperature adjusting means for setting the temperature of said at least one of said first and second monocrystal windows between the temperature of liquid nitrogen and 150° C.; and output means coupled to an output of said photo-electron multiplier for measuring the intensity of the electrons collected by said collector.

7. A photo-detector as defined by claim 6 wherein said second monocrystal window has a third KCl film deposited thereon.

8. A photo-detector as defined by claim 6 wherein said output means comprises a pulse counter circuit coupled to said photo-electron multiplier by an amplifier.

* * * * *